United States Patent [19]

Fujioka et al.

[11] Patent Number: 4,539,142
[45] Date of Patent: Sep. 3, 1985

[54] 4-(2-BORNYLOXY)-2-BUTYN-1-OL AND ORGANOLEPTIC USES THEREOF

[75] Inventors: Futoshi Fujioka, Wanamassa; Richard M. Boden, Ocean; William L. Schreiber, Jackson, all of N.J.

[73] Assignee: International Flavors & Fragrances Inc., New York, N.Y.

[21] Appl. No.: 604,230

[22] Filed: Apr. 26, 1984

Related U.S. Application Data

[63] Continuation-in-part of Ser. No. 574,150, Jan. 26, 1984, Pat. No. 4,521,634, which is a continuation-in-part of Ser. No. 533,915, Sep. 19, 1983, , which is a continuation-in-part of Ser. No. 507,292, Aug. 1, 1983, abandoned.

[51] Int. Cl.³ ............................ A61K 7/46; C07C 5/23
[52] U.S. Cl. ................................ 252/522 R; 568/665; 252/522 A; 252/8.6; 252/174.11; 514/951
[58] Field of Search ................. 568/665; 252/522 R, 252/522 A, 8.6, 174.11; 514/951

[56] References Cited

U.S. PATENT DOCUMENTS 3,354,225 11/1967 Kane ............................. 252/522 R Primary Examiner—Anton H. Sutto
Attorney, Agent, or Firm—Arthur L. Liberman

[57] ABSTRACT

Described is the 4-(2-bornyloxy)-2-butyn-1-ol of our invention defined according to the structure:

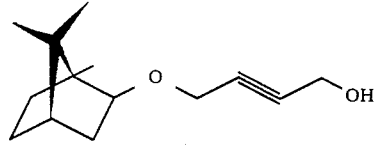

as well as methods for augmenting or enhancing the aroma of consumable materials including perfumes, colognes and perfumed articles by adding thereto an aroma augmenting or enhancing quantity of the 4-(2-bornyloxy)-2-butyn-1-ol of our invention.

7 Claims, 3 Drawing Figures

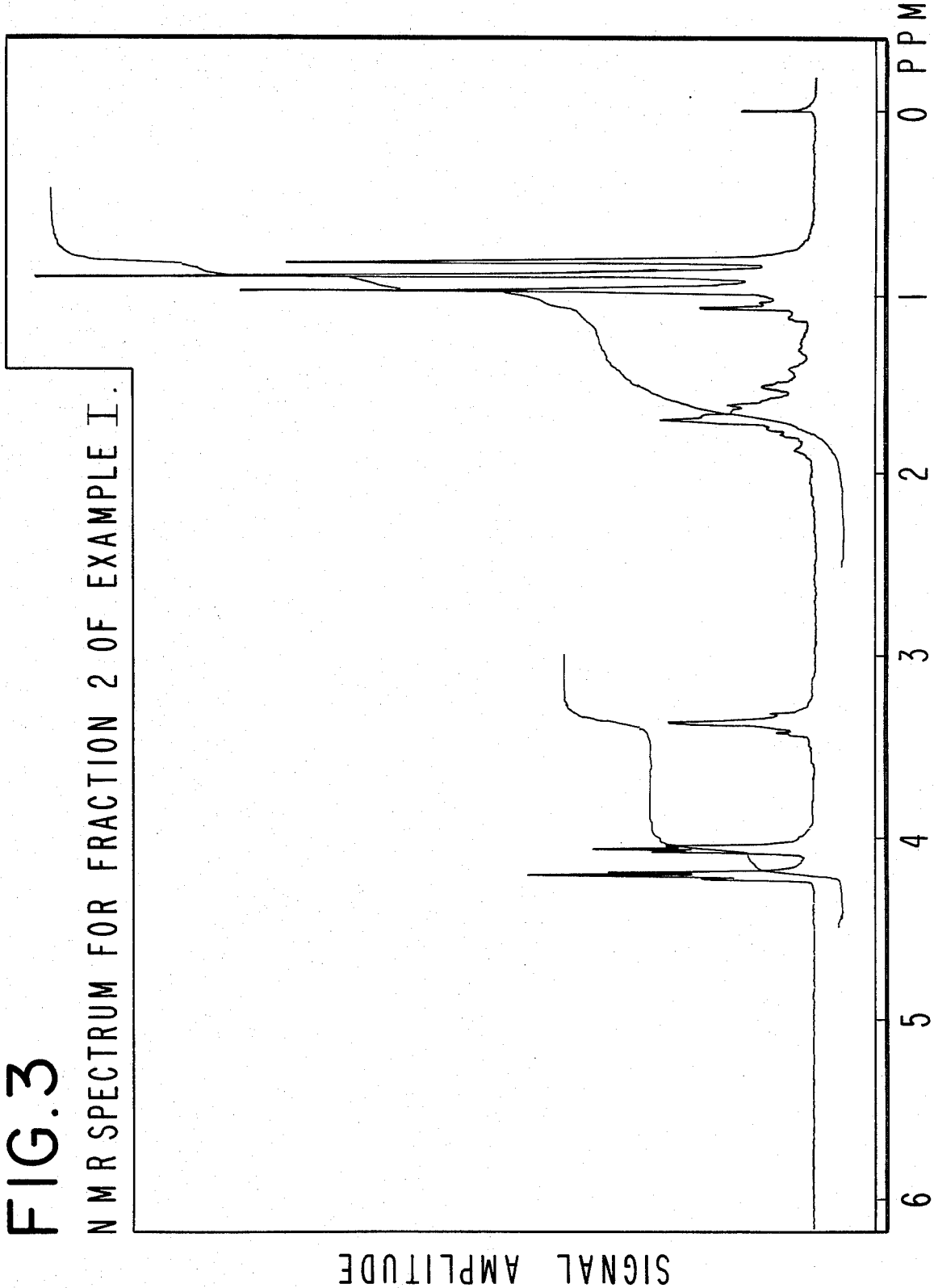
FIG. 3 NMR SPECTRUM FOR FRACTION 2 OF EXAMPLE I.

4-(2-BORNYLOXY)-2-BUTYN-1-OL AND ORGANOLEPTIC USES THEREOF

This application is a continuation-in-part of application for U.S. Letters Patent, Ser. No. 574,150 filed on Jan. 26, 1984, now U.S. Pat. No. 4,521,634 which, in turn, is a continuation-in part of application for U.S. Letters Patent, Ser. No. 533,915 filed on Sept. 19, 1983, which, in turn, is a continuation-in-part of application for U.S. Letters Patent, Ser. No. 507,292 filed on Aug. 1, 1983, abandoned.

BACKGROUND OF THE INVENTION

The instant invention provides the 4-(2-bornyloxy)-2-butyn-1-ol of our invention defined according to the structure:

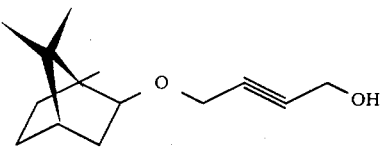

as well as the use thereof for augmenting or enhancing the aroma of perfume compositions, colognes and perfumed articles.

Inexpensive woody, patchouli-like aromas with woody, camphoraceous, patchouli-like and cedar-like topnotes are highly desirable in the art of perfumery. Many of the natural materials which provide such fragrances and contribute desired nuances to perfumery compositions as well as perfumed articles including solid or liquid anionic, cationic, nonionic or zwitter-ionic detergents, perfumed polymers, fabric softener compositions, fabric softener articles, hair preparations, cosmetic powders and the like are high in cost, vary in quality from one batch to another and/or are generally subject to the usual variations of natural products.

Nothing in the prior art suggests the 4-(2-bornyloxy)-2-butyn-1-ol of our invention or organoleptic uses of same.

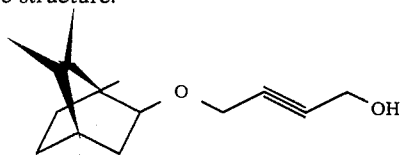

(conditions: SE-30 column programmed at 100°–220° C. at 8° C. per minute).

Figure 2:
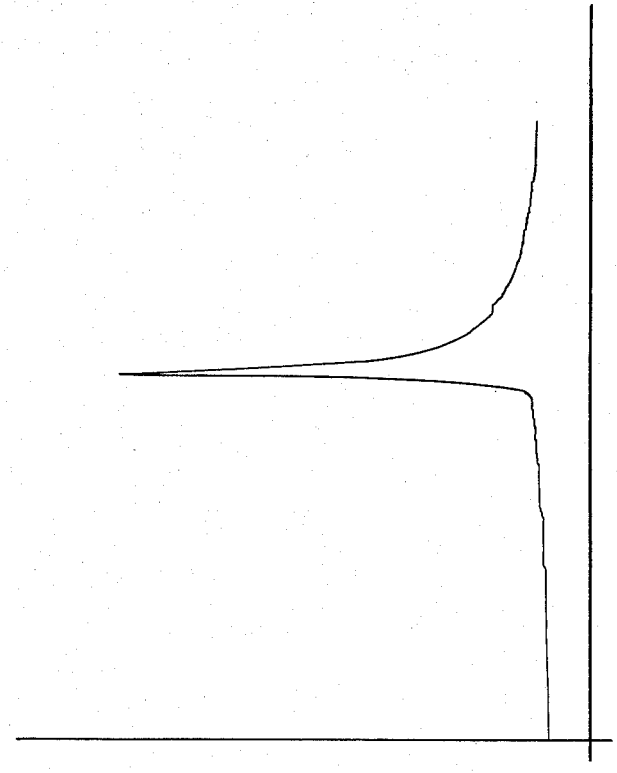

FIG. 2 is the GLC profile for bulked Fractions 2 and 3 of the first distillation of the reaction product of Example I containing the compound having the structure:

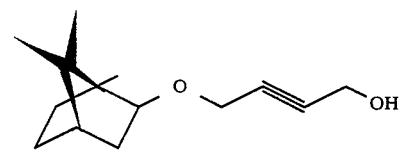

(conditions: SE-30 column programmed at 100°–220° C. at 8° C. per minute).

FIG. 3 is the NMR spectrum for Fraction 2 of the second distillation of the reaction product of Example I containing the compound having the structure:

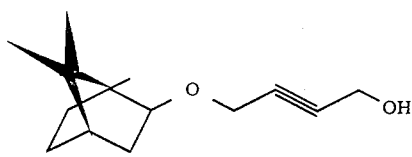

(conditions: Field strength: 100 MHz; Solvent: $CFCl_3$).

THE INVENTION

The present invention provides the 4-(2-bornyloxy)-2-butyn-1-ol having the structure:

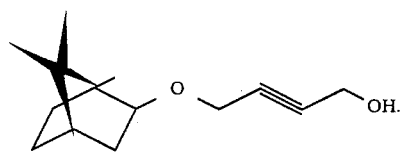

The present invention also provides a process for preparing the 4-(2-bornyloxy)-2-butyn-1-ol by reacting camphene with 1,4-dihydroxy-2-butyne in the presence of an appropriate catalyst to form the 4-(2-bornyloxy)-2-butyn-1-ol of our invention in accordance with the reaction:

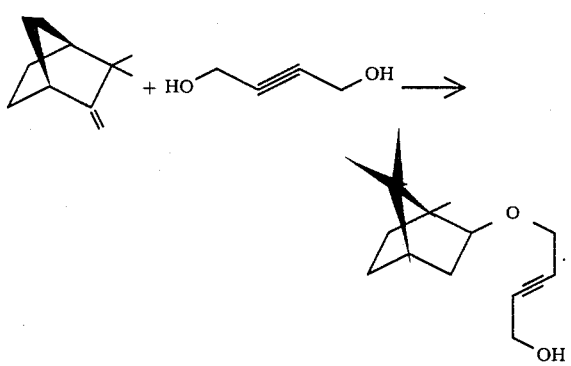

Thus, the process of our invention involves the reaction of camphene defined according to the structure:

with 1,4-dihydroxy-2-butyne having the structure:

The resulting 4-(2-bornyloxy)-2-butyn-1-ol of our invention having the structure:

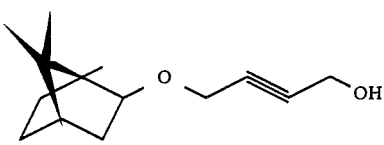

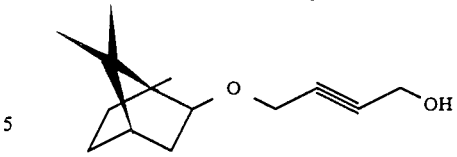

produced according to the process of our invention is capable of augmenting or enhancing woody, patchouli-like aromas with woody, camphoraceous, patchouli-like and cedar-like topnotes of perfume compositions, colognes and perfumed articles (including soaps, anionic, cationic, nonionic or zwitterionic detergents, fabric softener compositions, fabric softener articles, optical brightener compositions, perfumed polymers, hair preparations and the like) thus fulfilling a need in the field of perfumery as well as detergents, colognes, fabric softeners and cosmetics manufacture.

The reaction of camphene with the 1-4-dihydroxy-2-butyn, to wit:

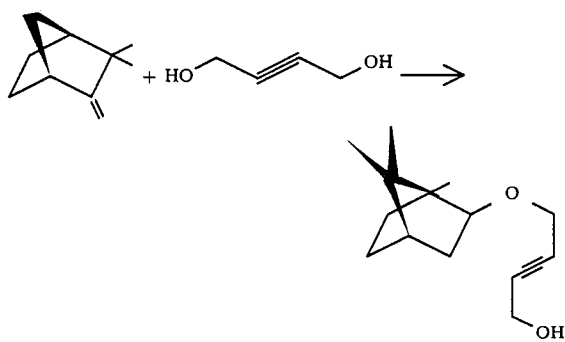

takes place in the presence of a catalyst which is a Lewis acid, for example, boron trifluoride etherate at temperatures in the range of from about 60° C. up to about 100° C. and at pressures in the range of from about 1 atmosphere up to about 10 atmospheres. Preferably, the reaction takes place at 80° C. at atmospheric pressure and at reflux conditions. The reaction time may vary from about two hours up to about twenty hours depending upon the temperature of reaction. Higher temperatures of reaction give rise to lower times of reaction and lower temperatures of reaction require higher times of reaction but a better overall yield. The mole ratio of 1,4-dihydroxy-2-butyn having the structure:

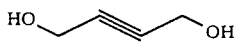

to camphene having the structure:

may vary from about 1:2 up to about 3:1 with a mole ratio of diol:camphene of about 2:1 being preferred. At the end of the reaction, the reaction mass is neutralized and the reaction product defined according to the structure:

is purified for ultimate utility as a perfumant as by means of fractional distillation.

The 4-(2-bornyloxy)-2-butyn-1-ol prepared in accordance with the process of our invention and one or more auxiliary perfume ingredients including, for example, alcohols, other than the 4-(2-bornyloxy)-2-butyn-1-ol of our invention, ketones, aldehydes, terpinic hydrocarbons, nitriles, esters, lactones, natural essential oils and synthetic essential oils may be admixed so that the combined odors of the individual components produce a pleasant and desired fragrance, particularly and preferably in woody and patchouli fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however, the overall sensory effect of the perfume composition will be at least the sum total of the effects of each of the ingredients. Thus, the 4-(2-bornyloxy)-2-butyn-1-ol of our invention prepared in accordance with the process of our invention can be used to alter, modify or enhance the aroma characteristics of a perfume composition, for example, by utilizing or moderating the olfactory reaction contributed by another ingredient in the composition.

The amount of the 4-(2-bornyloxy)-2-butyn-1-ol of our invention prepared in accordance with the process of our invention, which will be effective in perfume compositions as well as perfumed articles (e.g., anionic, cationic, nonionic or zwitterionic solid or liquid detergents, soaps, fabric softener compositions, drier-added fabric softener articles, optical brightener compositions, perfumed polymers, textile sizing agents and the like) and colognes depends on many factors, including the other ingredients, their amounts and the effects which are desired. It has been found that perfume compositions containing as little as 0.01% of the 4-(2-bornyloxy)-2-butyn-1-ol of our invention or even less (e.g., 0.005%) can be used to impart, augment or enhance woody and patchouli-like aromas with woody, camphoraceous, patchouli-like and cedar-like topnotes in or to soaps, cosmetics, solid or liquid anionic, cationic, nonionic or zwitterionic detergents, fabric softener compositions, fabric softener articles, optical brightener compositions, textile sizing compositions, perfumed polymers or other products. The amount employed can range up to 70% of the fragrance components and will depend on considerations of cost, nature of the end product, the effect desired on the finished product and the particular fragrance sought.

The 4-(2-bornyloxy)-2-butyn-1-ol of our invention is useful (taken alone or together with other ingredients in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders and perfumed polymers and articles of manufacture produced from said perfumed polymers, e.g., garbage bags, children's toys and the like. When used as an olfactory component in perfumed articles, as little as 0.1% of the 4-(2-bornyloxy)-2-butyn-1-ol of our invention prepared in accordance with the process of our invention will suffice to impart, augment or enhance woody, and patchouli-like aromas with woody, camphoraceous, patchouli-like and cedar topnotes. Generally, no more than 6% of the 4-(2-bornyloxy)-2-butyn-1-ol of our invention based on the ultimate end product is required in the perfumed article. Accordingly, the range of 4-(2-bornyloxy)-2-butyn-1-ol in the perfumed article is from about 0.1% by weight of the 4-(2-bornyloxy)-2-butyn-1-ol up to about 6% by weight of the 4-(2-bornyloxy)-2-butyn-1-ol based on the total weight of the perfumed article.

In addition, the perfume composition or fragrance composition of our invention can contain a vehicle or carrier for the 4-(2-bornyloxy)-2-butyn-1-ol. The vehicle can be a liquid such as a non-toxic alcohol, e.g., ethyl alcohol, a non-toxic glycol, e.g., propylene glycol or the like. The carrier can also be an absorbent solid, such as a gum (e.g., gum arabic, guar gum, xanthan gum) or components for encapsulating the composition (such as, for example, gelatin as by coacervation or such as a urea formaldehyde prepolymer which on polymerization forms a capsule shell around a liquid perfume center).

Our invention also relates to the utilization of controlled release technology for the controlled release of perfumes into gaseous environments from polymers such as mixtures of epsilon polycaprolactone polymers and polyethylene which polyepsilon caprolactone polymers are defined according to at least one of the structures:

with the term $\eta$ being the average number of repeating monomeric units for the epsilon polycaprolactone polymer. The perfumed material's release rate from such polymer mixture is close to "zero order". As a general rule, the release rate in a polymeric matrix is proportional to $t^{-\frac{1}{2}}$ until about 60% of the functional fluid is released from the polymeric matrix. The release rate thereafter is related exponentially to time as a general rule according to the equation:

$$\frac{dM_t}{dt} = k_1 e^{-k_2 t}$$

wherein $k_1$ and $k_2$ are constants. According to Kydonieus, "Controlled Release Technologies: Methods, Theory, and Applications" (cited, supra) the amount of perfume composition released is proportional to time as long as the concentration of perfume material present, e.g., the 4-(2-bornyloxy)-2-butyn-1-ol of our invention is higher than the solubility of the agent in the matrix. Thus, such dispersed systems are similar to the dissolved systems except that instead of a decreased release rate after 60% of the perfume material has been emitted, the relationship holds almost over the complete release curve. Kydonieus further states, that if one assumes that the release of functional fluid by diffusion is negligible in monolithic erodible systems, the speed of erosion will control the release rate and release by erosion by a surface-area-dependent phenomenon, the release being constant (zero order) as long as the surface area does not change during the erosion process. This is the case with the polymers containing the 4-(2-bornyloxy)-2-butyn-1-ol of our invention.

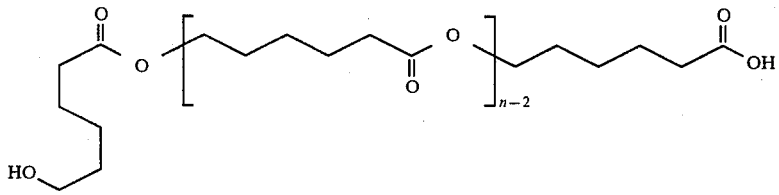

and/or

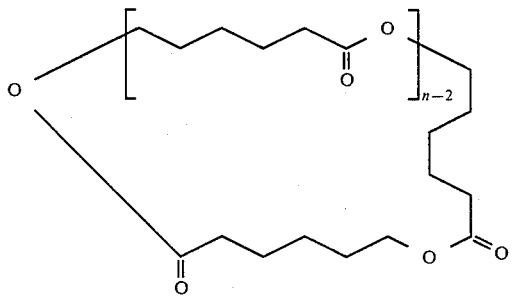

wherein "n" is from about 50 up to about 1,200 with the proviso that the average "n" in the system varies from about 150 up to about 700 according to the mathematical statement:

$[700 \geq \eta \geq 150]$

The polyepsilon caprolactone polymers useful in practicing our invention are more specifically described in the brochure of the Union Carbide Corporation, 270 Park Avenue, New York, N.Y. 10017, entitled "New Polycaprolactone Thermoplastic Polymers PCL-300 and PCL-700". These polyepsilon caprolactone polymers are composed of a repeating sequence of non-polar methylene groups and relatively polar ester groups. The average number of repeating monomeric units varies between 150 and 700 depending on the particular "PCL" number. Thus, regarding PCL-300 the average number of repeating monomeric units is 300. Regarding PCL-700, the average number of repeating monomeric units is 700.

The polyepsilon caprolactone homopolymers which are ultimately taken in admixture with such materials as polyethylene useful in the practice of our invention may also be stabilized using stabilizers as defined in U.S. Pat. No. 4,360,682 issued on Nov. 23, 1982, the specification for which is incorporated herein by reference. The stabilizing materials which stabilized the polyepsilon caprolactone useful in conjunction with our invention against discoloration are dihydroxybenzenes such hydroquinone or compounds having the formula:

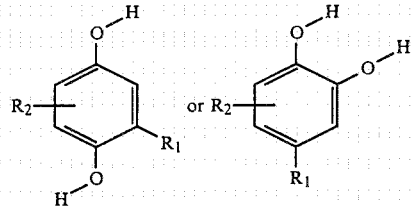

in which $R_1$ is alkyl of from 1 to 8 carbon atoms, and $R_2$ is hydrogen or alkyl of 1 to 8 carbon atoms. It is preferable to have such stabilizer in the polyepsilon caprolactone homopolymer in an amount of from about 100 to 500 ppm. Such stabilizers do not interfere with the functional fluids dissolved and/or absorbed into the polymeric matrix.

The method of incorporating the 4-(2-bornyloxy)-2-butyn-1-ol of our invention or perfume compositions containing same into the polymers may be according to the techniques of U.S. Pat. No. 3,505,432 issued on Apr. 7, 1970 (the specification for which is incorporated by reference herein) or U.S. Pat. No. 4,247,498 issued on Jan. 27, 1981, the disclosure of which is incorporated by reference herein.

Thus, for example, a first amount of liquid polyethylenepolyepsilon caprolactone polymer mixture (50:50) is mixed with the 4-(2-bornyloxy)-2-butyn-1-ol of our invention. Drops are formed from the mixture and the drops are then melted, if desired, with a second amount of unscented low density polyethylene, for example, or polypropylene, for example. Usually, but not necessarily, the second amount of polymer is larger than the first amount. The resulting mixture thus obtained, is solidified subsequent to or prior to ultimate casting into a utilitarian shape.

Thus, in accordance with one aspect of our invention, the imparting of scent is effected in two stages. In a first stage, a 50:50 (weight:weight) polyepsilon caprolactone, e.g., PCL-700: polyethylene in molten form is admixed with a high percentage of the 4-(2-bornyloxy)-2-butyn-1-ol of our invention and the mixture is solidified in the form of pellets or beads. These pellets or beads thus contain a high percentage of the 4-(2-bornyloxy)-2-butyn-1-ol (e.g., up to 45% by weight of the entire mixture) and may be used as "master pellets" which thereafter, in a second stage, if desired, may be admixed and liquified with additional polymers such as additional polyethylene or mixtures of polyethylene and polyepsilon caprolactone in an unscented state, or unscented polypropylene. In addition, additional polymers or copolymers may be used, for example, copolymers specified and described in United Kingdom Patent Specification No. 1,589,201 published on May 7, 1981, the specification for which is incorporated by reference herein.

In accordance with the present invention the 4-(2-bornyloxy)-2-butyn-1-ol of our invention is added to the polymer in a large closed container or drum which is maintained under controlled temperature conditions while the polymer in a melted condition is mixed with the 4-(2-bornyloxy)-2-butyn-1-ol under agitation.

In order that the perfume be added uniformly to the polymer, the temperature of the melt is constantly controlled during the process. The polymer-perfume mixture is then directed through an elongated conduit or pipe element having a plurality of orifices adjacent to the lower most portion thereof. The polymer enriched by the 4-(2-bornyloxy)-2-butyn-1-ol of our invention is permitted to drip through the orifices onto a continuously moving, cooled conveyor upon which the polymer containing the 4-(2-bornyloxy)-2-butyn-1-ol of our invention solidifies into small size pellets with the perfume imprisoned therein. The apparatus useful in conjunction with this process, advantageously includes a conveyor of a material which will not adhere to the polymer which contains the 4-(2-bornyloxy)-2-butyn-1-ol of our invention.

In order that droplets form into uniform pellets or beads, the conveyor is continuously washed with a liquid, such as water to maintain the surface relatively cool. The pellets are delivered by the conveyor into a container and packaged for shipment.

The following Example I illustrates a process for preparing the 4-(2-bornyloxy)-2-butyn-1-ol of our invention having the structure:

Examples II, et seq are illustrative of the organoleptic utilities of the 4-(2-bornyloxy)-2-butyn-1-ol of our invention.

All parts and percentages given herein are by weight unless otherwise specified.

EXAMPLE I

Preparation of 4-(2-bornyloxy)-2-butyn-1-ol

Reaction:

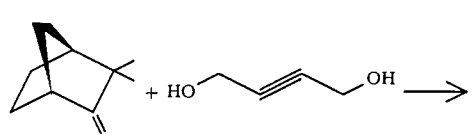

-continued

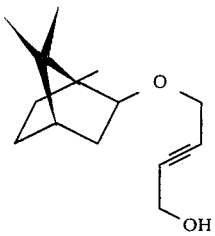

Into a 5-liter reaction vessel equipped with stirrer, thermometer, reflux condenser and heating mantle are placed 2510 grams of camphene (14.76 moles) and 1188 grams of 2-butyne-1,4-diol (16.97 moles). The reaction mass is heated to 56° C. and over a period of 15 minutes, 2 ml of boron trifluoride is added thereto. The reaction mass is then heated to reflux (135° C.) and refluxed for a period of ten hours. At the end of the ten hour period, an additional 10 ml BF 3 is added and the reaction mass is heated to reflux for an additional three hours. The reaction mass is then cooled and the crude reaction product is washed with saturated sodium carbonate solution until neutral. The aqueous phase is separated from the organic phase. The aqueous phase is extracted with toluene and the toluene extracts are added to the organic phase. The resulting organic material is then charged to an evaporator and the toluene solvent is recovered.

The resulting product is then distilled on a splash column packed with saddles yielding the following fractions:

| Fraction No. | Vapor Temp. (°C.) | Liquid Temp. (°C.) | Vacuum mm/Hg. Pressure |
|---|---|---|---|
| 1 | 25/140 | 94/164 | 1.6/1.6 |
| 2 | 150 | 183 | 9.4 |
| 3 | 155 | 196 | 1.4 |
| 4 | 172 | 210 | 1.4 |

Fractions 2, 3 and 4 are bulked and redistilled on a 12″ Goodloe column yielding the following fractions:

| Fraction No. | Vapor Temp. (°C.) | Liquid Temp. (°C.) | Vacuum mm/Hg. Pressure | Reflux Ratio R/D |
|---|---|---|---|---|
| 1 | 89/133 | 177/172 | 1.6 | 7.3 |
| 2 | 139 | 175 | 1.5 | 7.3 |
| 3 | 139 | 179 | 1.4 | 7.3 |
| 4 | 140 | 179 | 1.4 | 7.3 |
| 5 | 140 | 182 | 1.4 | 7.3 |
| 6 | 140 | 180 | 1.4 | 7.3 |
| 7 | 138/140 | 187/190 | 1.6 | 7.3 |
| 8 | 140 | 175 | 1.6 | 7.3 |
| 9 | 140 | 185 | 1.6 | 7.3 |
| 10 | 140 | 190 | 1.6 | 7.3 |
| 11 | 140 | 190 | 1.6 | 7.3 |
| 12 | 138 | 178 | 1.3 | 7.3 |
| 13 | 138 | 178 | 1.3 | 7.3 |
| 14 | 141 | 190 | 1.3 | 7.3 |
| 15 | 142 | 197 | 1.3 | 7.3 |
| 16 | 147 | 210 | 1.3 | 7.3 |
| 17 | 144 | 216 | 1.3 | 7.3 |

Bulked Fractions 3–16 have an excellent woody and patchouli aroma which is very long-lasting with excellent woody, camphoraceous, patchouli-like and cedar nuances.

Figure 1:
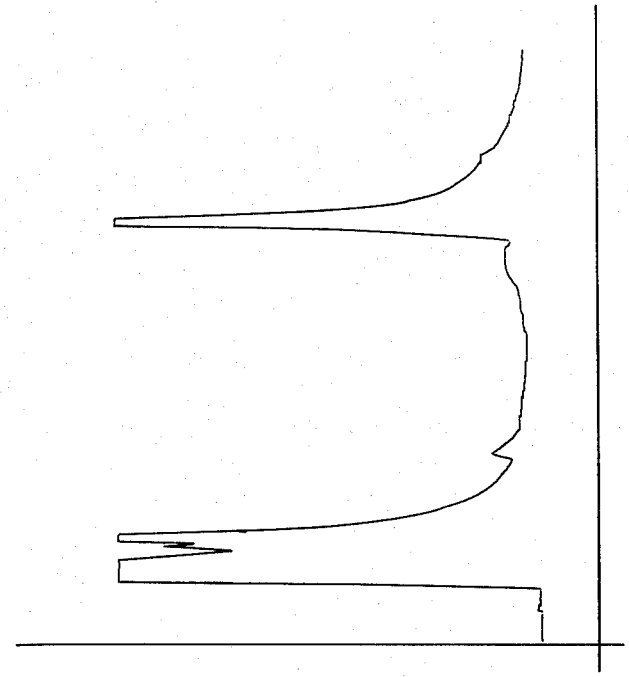
FIG. 1 is the GLC profile for the crude reaction product of Example I containing the compound having the structure.

FIG. 1 is the GLC profile for the crude reaction product prior to distillation (conditions: SE-30 column programmed at 100°–220° C. at 8° C. per minute).

FIG. 2 is the GLC profile for bulked Fractions 2 and 3 of the first distillation (conditions: SE-30 column programmed at 100°–220° C. at 8° C. per minute).

FIG. 3 is the NMR spectrum for Fraction 2 of the second distillation (conditions: Field strength: 100 MHz; Solvent: CFCl$_3$).

EXAMPLE II

Perfume Formulation

The following woody cologne, perfume formulation is prepared:

| Ingredients | Parts by Weight |
|---|---|
| Bergamot oil | 150 |
| Orange oil | 200 |
| Lemon oil | 50 |
| Eugenol | 10 |
| 4-(4-methyl-4-hydroxy amyl) Δ$^3$ cyclohexene carboxaldehyde | 40 |
| Ylang oil | 2 |
| Petitgrain Paraguay | 10 |
| Gamma methyl ionone | 20 |
| Vetiver Venezuela | 18 |
| 3α-Methyl-dodecahydro-6,6,9a-trimethylnaptho-[2,1-b] furan | 5 |
| Product produced by the reaction of acetic anhydride, polyphosphoric acid and 1,5,9-trimethyl cyclododecatriene-1,5,9 according to the process of Example I of U.S. Letters Patent 3,718,697, the specification for which is incorporated by reference herein | 5 |
| Octahydro-9,9-dimethyl-1,6-methano-naphthalene-1-(2H)—ol produced according to Example III of U.S. Letters Patent 3,996,169, the specification for which is incorporated by reference herein | 50 |
| The compound having the structure: 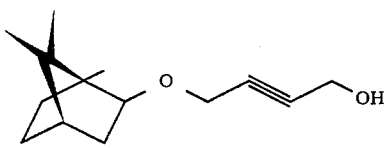 prepared according to Example I bulked Fractions 3–16 | 12 |

The compound having the structure:

prepared according to Example I imparts an excellent long-lasting woody, patchouli-like aroma to this "woody cologne" composition. Accordingly, the composition can be described as "woody cologne" with woody and patchouli-like undertones and woody, camphoraceous, patchouli-like and cedar topnotes.

EXAMPLE III

Preparation of Cosmetic Powder Compositions

Cosmetic powder compositions are prepared by mixing in a ball mill 100 grams of talcum powder with 0.25 grams of each of the substances set forth in Table I below. Each of the cosmetic powder compositions has an excellent aroma as described in Table I below:

TABLE I

| Substance | Aroma Description |
|---|---|
| Compound having the structure: 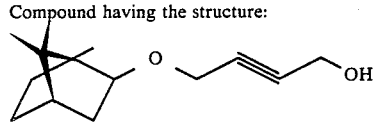 produced according to Example I bulked Fractions 3-16 of second distillation. | A woody and patchouli aroma with woody, camphoraceous, patchouli-like and cedar topnotes. |
| Perfume composition of Example II. | A "woody cologne" with woody and patchouli-like undertones and woody, camphoraceous patchouli-like and cedar topnotes. |

EXAMPLE IV

Perfumed Liquid Detergent

Concentrated liquid detergents with aromas as set forth in Table I of Example III (which detergents are prepared from Lysine salt of n-dodecyl benzene sulfonic acid as more specifically described in U.S. Letters Patent, Ser. No. 3,948,818 issued on Apr. 6, 1976, the specification for which is incorporated by reference herein) are prepared containing each of the substances set forth in Table I of Example III, supra. They are prepared by adding and homogeneously mixing the appropriate quantity of perfumery substance as set forth in Table I of Example III in the liquid detergent. The detergents all possess aromas as set forth in Table I of Example III the intensity increasing with greater concentrations of perfumery substance of Table I of Example III, supra.

EXAMPLE V

Preparation of a Cologne and Handkerchief Perfume

The perfume substances of Table I of Example III, supra are incorporated into colognes at concentrations of 1.5%, 2.0%, 2.5%, 3.0% and 4.0% in 80%, 85%, and 90% aqueous ethanol; and into a handkerchief perfume composition at concentrations of 10%, 15%, 20%, 25% and 30% (in 85%, 90% and 95% aqueous ethanol). Distinct and definitive aromas as set forth in Table I of Example III are imparted to the cologne and to the handkerchief perfume compositions.

EXAMPLE VI

Preparation of a Detergent Composition

A total of 100 grams of a detergent powder (a nonionic detergent powder containing a proteolytic enzyme prepared according to Example I of Canadian Letters Patent No. 985,190 issued on Mar. 9, 1976, the disclosure of which is incorporated by reference herein) is mixed with 0.15 grams of each of the substances set forth in Table I of Example III, supra, until substantially homogeneous compositions are obtained. These compositions have excellent aromas as set forth in Table I of Example III.

EXAMPLE VII

Preparation of Soap

Each of the perfumery substances of Table I of Example III are incorporated into soap (LVU-1) at 0.1% by weight of each substance. After two weeks in the oven at 90° F., each of the soaps showed no visual effect from the heat. Each of the soaps manifested an excellent aroma as set forth in Table I of Example III, supra.

EXAMPLE VIII

Preparation of Soap Composition

One hundred grams of soap chips (IVORY ®, registered trademark of the Procter & Gamble Co. of Cincinnati, Ohio) are mixed individually with one gram each of the perfumery substances of Table I of Example III, supra, until a homogeneous composition is obtained. The homogeneous composition is then treated under three atmospheres pressure at 180° C. for a period of three hours and the resulting liquid is placed into a soap mold. The resulting soap cakes, on cooling, manifest excellent aromas as set forth in Table I of Example III, supra.

EXAMPLE IX

Preparation of a Solid Detergent Composition

A detergent is prepared from the following ingredients according to Example I of Canadian Letters Patent No. 1,007,948, the specification for which is incorporated by reference herein:

| Ingredients | Parts by Weight |
|---|---|
| "Neodol 45-II" (a $C_{14}$–$C_{15}$ (alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed separately with 0.15 grams of each of the perfume substances of Table I of Example III, supra. The detergent samples each have excellent aromas as set forth in Table I of Example III, supra.

EXAMPLE X

Utilizing the procedure of Example 1 at column 15 of U.S. Pat. No. 3,632,396 (the specification for which is incorporated by reference herein), a non-woven cloth substrate useful as a dryer-added fabric softening article of manufacture is prepared, wherein the substrate, the substrate coating and the outer coating and the perfuming material are as follows:
1. a water "dissolvable" paper ("Dissolvo Paper")
2. Adogen 448 (m.p. about 140° F.) as the substrate coating; and
3. an outer coating having the following formulation (m.p. about 150° F.);
   57 percent $C_{20-22}$HAPS
   22 percent isopropyl alcohol
   20 percent antistatic agent
   1 percent of one of the perfume substances of Table I of Example III, supra.

A fabric softening composition prepared as set forth above having the above aroma characteristics as set forth in Table I of Example III, supra, essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of substrate. The aroma set forth in Table I of Example III is imparted in a pleasant manner to the headspace in the dryer on operation thereof, using said dryer-added fabric softening non-woven fabric.

What is claimed is:

1. The 4-(2-bornyloxy)-2-butyn-1-ol having the structure:

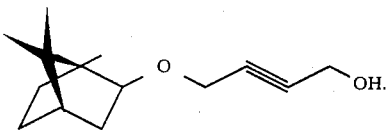

2. A process for augmenting or enhancing the aroma of a consumable material selected from the group consisting of perfume compositions, colognes and perfumed articles comprising the step of intimately admixing with said consumable material an aroma augmenting or enhancing quantity of the 4-(2-bornyloxy)-2-butyn-1-ol defined according to claim 1.

3. The process of claim 2 wherein the consumable material is a perfume composition or cologne.

4. The process of claim 2 wherein the consumable material is a perfumed article and the perfumed article is a solid or liquid anionic, cationic, nonionic or zwitterionic detergent.

5. The process of claim 2 wherein the consumable material is a perfumed article and the perfumed article is a perfumed polymer.

6. The process of claim 2 wherein the consumable material is a perfumed article and the perfumed article is a fabric softener composition or drier-added fabric softener article.

7. The process of claim 2 wherein the consumable material is a perfumed article and the perfumed article is a cosmetic powder.

* * * * *